(12) United States Patent
Nies et al.

(10) Patent No.: US 7,578,845 B2
(45) Date of Patent: Aug. 25, 2009

(54) STRUCTURED COMPOSITES AS A MATRIX (SCAFFOLD) FOR THE TISSUE ENGINEERING OF BONES

(75) Inventors: Berthold Nies, Fraenkisch-Crumbach (DE); Brigitte Jeschke, Kelkheim (DE); Patricia Schaffner, Griosheim (DE)

(73) Assignee: Biomet Deutschland GmbH, Berlin (DE)

( * ) Notice: Subject to any disclaimer, the term of this patent is extended or adjusted under 35 U.S.C. 154(b) by 0 days.

(21) Appl. No.: 10/512,763

(22) PCT Filed: Apr. 7, 2003

(86) PCT No.: PCT/EP03/03582

§ 371 (c)(1),
(2), (4) Date: May 9, 2005

(87) PCT Pub. No.: WO03/092760

PCT Pub. Date: Nov. 13, 2003

(65) Prior Publication Data

US 2005/0233454 A1    Oct. 20, 2005

(30) Foreign Application Priority Data

Apr. 29, 2002    (DE) ............................ 102 19 183

(51) Int. Cl.
*A61F 2/28* (2006.01)
(52) U.S. Cl. ............................................. 623/16.11
(58) Field of Classification Search ............ None
See application file for complete search history.

(56) References Cited

U.S. PATENT DOCUMENTS

| | | | |
|---|---|---|---|
| 4,774,227 A | 9/1988 | Piez et al. | |
| 4,795,467 A | 1/1989 | Piez et al. | |
| 4,865,602 A | 9/1989 | Smestad et al. | |
| 5,231,169 A | 7/1993 | Constantz et al. | |
| 5,246,457 A | 9/1993 | Piez et al. | |
| 5,320,844 A | 6/1994 | Liu | |
| 5,338,772 A | 8/1994 | Bauer et al. | |
| 5,356,629 A | 10/1994 | Sander et al. | |
| 5,455,231 A | 10/1995 | Constantz et al. | |
| 6,511,510 B1 | 1/2003 | de Bruijn et al. | |
| 7,357,941 B2 | 4/2008 | Dalal et al. | |
| 2005/0124720 A1 | 6/2005 | Rizzoli et al. | |

FOREIGN PATENT DOCUMENTS

| | | |
|---|---|---|
| CA | 2282075 | 3/2000 |
| CA | 2439813 | 9/2002 |
| CA | 2481383 | 10/2003 |
| DE | 4120325 | 12/1992 |
| DE | 19811027 | 9/1998 |
| DE | 29922585 | 7/2000 |
| DE | 10219765 | 11/2002 |
| EP | 0197693 | 10/1986 |
| EP | 0270254 | 6/1988 |
| EP | 0233770 B1 | 5/1990 |
| EP | 0519293 | 12/1992 |
| EP | 1142695 | 10/2001 |
| WO | WO9301273 A1 | 1/1993 |
| WO | WO 97/14376 | 4/1997 |
| WO | WO 00/04940 | 2/2000 |
| WO | WO 00/07639 | 2/2000 |
| WO | WO0270029 A3 | 9/2002 |

OTHER PUBLICATIONS

The terms "sponge" and "like", Merrian-Webster Online Dictionary, at the web- http://www.m-w.com, p. 1-2.*

* cited by examiner

*Primary Examiner*—Irene Marx
*Assistant Examiner*—Satyendra K Singh
(74) *Attorney, Agent, or Firm*—Millen, White, zelano & Branigan, P.C.

(57) ABSTRACT

The invention relates to a structured composite as a carrier for the tissue engineering and implant material of bones, consisting of a mass of porous calcium phosphate granulates. The granulated material has a grain size of between 0.5 and 10 mm with macropores and micropores, and the macropores have an average diameter of between 50 and 500 ?m and are bound by a biocompatible binding agent.

11 Claims, No Drawings

STRUCTURED COMPOSITES AS A MATRIX (SCAFFOLD) FOR THE TISSUE ENGINEERING OF BONES

The invention describes a structured composite as support for tissue engineering and implant material of bones (in situ and in vitro) consisting of a mass of porous calcium phosphate granules having a particle size of from 0.5 to 10 mm with macropores and micropores, where the macropores have an average diameter of from 50 to 500 µm and are bound by a biocompatible binder.

A synthetic substitute for autologous bone or donated bone is becoming increasingly important because, on the one hand, the quality of the developed materials is increasingly satisfying the demands of the clients and, on the other hand, the disadvantages associated with the biological materials are avoided, such as, in particular, limited availability, removal problems in the case of autologous bone, risk of disease transmission in the case of donated bone.

Approaches for increasing the biological quality of the synthetic materials entail upgrading the bone substitute with recombinant growth factors, autologous growth factors (platelet preparations), adhesion factors (RGD peptides) and/ or autologous cell preparations (bone marrow aspirate).

There are in particular two development priorities for obtaining the desired properties of optimized bone substitute materials, firstly mechanical optimization for load-bearing applications and structural implants and secondly biological optimization with the aim of complete regeneration of full-quality bone tissue as quickly as possible (during which the mechanical function is taken over by metal implants).

The objective for biologically optimized bone regeneration products was for a long time concentrated on the development of recombinant bone growth factors (especially BMP2 and OP1/BMP7) and combination thereof with various support materials and functional implants, although in most cases the development of suitable support structures was pursued with a lower priority than that of the recombinant protein.

The objective has shifted increasingly in recent times, inter alia also because the recombinant growth factors were unable to satisfy the high expectations in clinical studies.

Attractive alternatives are to be seen in particular in the use of autologous factors such as, in particular, platelet preparations and the bone marrow aspirants which have osteogenic activity. Compared with the removal of autologous bone, it is relatively uncomplicated to obtain these components, and there is scarcely any limit on the amount. In addition, these factors are, unlike iliac crest spongiosa, relatively quickly regenerated and are thus available again for later procedures.

When these autologous factors are used, selection of the support materials has crucial importance. An ideal support for many areas of use of materials which promote bone regeneration has the following properties in particular:

All components are biocompatible

All components are osteoconductive, i.e. they form a guiderail for the bone which is to be formed anew.

All components are biodegradable, preferably by cellular processes which are also responsible for bone remodeling.

If the components have only limited or no biodegradability, they should be firmly incorporated into the bone substance which has formed.

Porous structure with interconnecting macropore system for capillaries to grow into the matrix High overall porosity for uptake of autologous factors Adequate mechanical properties, so that the pore system is retained even on exposure to pressure from adjacent connective tissue and is available for ingrowth of tissue at the site.

Flexibility of the support material for good adaptation to the implant contour and generally good manipulability.

Low immunogenicity.

Such an ideal support material is currently unavailable despite the diverse bone substitute materials on offer. In particular, the combination of high porosity and flexibility with, at the same time, resistance to pressure has not been achieved to date.

WO 97/14376 (Orquest Inc.) discloses a porous biodegradable matrix as bone substitute, which persists for 7 to 14 days after implantation. The composite forms a network of insoluble biopolymeric fibrils, calcium phosphate minerals and, inter alia, 30 to 80% by weight mineralized collagen. The particle size of the calcium phosphate material is 5 µm or less.

EP-197 693 and EP-270 254 (Collagen Corp.) describe a biocompatible collagen/calcium phosphate mixture, which consists essentially of 60 to 98% by weight calcium phosphate mineral with admixture of 2 to 40% by weight of a reconstituted atelopeptide fibrillar collagen. The particle size of the calcium phosphate is 100 to 2000 µm.

It was an object of the present invention to achieve, on the basis of known and proven components, a material having the abovementioned properties.

It has now been found, surprisingly, that porous granules of calcium phosphate can be mixed with biocompatible binders, preferably collagen suspensions, and that composites which comply with the requirements can be produced from these suspensions by freeze drying.

The present invention thus relates to a structured composite as support for tissue engineering and implant material of bones consisting of a mass of porous calcium phosphate granules, characterized in that the granules have a particle size of from 0.5 to 10 mm with macropores and micropores, where the macropores have an average diameter of from 50 to 500 µm and are bound by a biocompatible binder.

The micropores preferably have an average diameter of from 0.5 to 5 µm.

The binder preferably consists of collagen or hyaloronic acid and can also be in crosslinked form.

The individual granules in this composite are uniformly distributed for example in a collagen fabric. The pore system is achieved in the granules and in the collagen fabric. Owing to the resistance of the granules to pressure, the composite cannot be compressed, which property is particularly crucial in applications in which the material is placed on a bone bed and adjoins soft tissue on one side, and is thus exposed to a soft tissue pressure. Such cases are very frequent in particular in the area of spinal surgery.

The composite consists according to the invention of porous calcium phosphate granules having a size of the granular particles of from 0.5 to 10 mm, preferably 1 to 4 mm. It is further preferred for there to be a uniform distribution of sizes of the granules in the particular composite, e.g. 2.0 to 3.2 mm particle size. The granules consist of one of the calcium phosphates used for bone substitutes. Endobon® or Calcibon® granules are preferably used. However, it is also possible to employ glass ceramics. Especially in the case of coarse granules, i.e. having a particle size of 2 mm upwards, the porosity of the individual particles should be interconnecting, i.e. the existing pores within the individual particles must be connected to one another.

The composite preferably comprises from 0.2 to 10% by weight, more preferably from 0.2 to 2% by weight, of binder, based on the composite.

The binder has the particular function of connecting the granular particles to one another and of absorbing the autologous factors like a sponge so that an optimal localization thereof for the application is possible. No pronounced swelling takes place, so that manipulability is facilitated. It serves further to simplify the manipulation of the granular material by preventing dislocation of the individual particles during the operation and in the first few days thereafter.

The binders particularly used are those collagens which are also already employed in the art in or as medical devices, in particular type I collagens and mixtures of type I and III. The origin may be either animal, human or recombinant. Fibrillar collagen of non-bovine but animal origin is preferred.

The composites can be loaded with autologous factors such as growth factors, platelet preparations and/or autologous cell preparations and/or cell extracts/protein preparations and then also release these to the bone.

It is also preferred for the composite to be loaded with recombinant factors or fragments thereof, such as growth factors, adhesion proteins and/or adhesion peptides. Loading with antibiotics is additionally preferred.

It is likewise conceivable to employ crosslinked gelatin in place of collagen.

The present invention also relates to a process for producing a structured composite as support for tissue engineering and implant material of bones, characterized by the following features:

mixing of a solution or suspension of binder with calcium phosphate granules having a particle size of from 0.5 to 10 mm with macropores and micropores, where the macropores have an average diameter of from 50 to 500 µm;

subsequent deep freezing and thawing, and freeze drying of the mixture under standard conditions.

A subsequent chemical crosslinking is also preferred.

The present invention also relates to the use of the structured composite of the invention as filling material in the area of spinal, oral or facial surgery. The invention is described in more detail and explained below by means of an exemplary embodiment.

EXEMPLARY EMBODIMENT

1. Production

The composite can be produced in various sizes. A composite 8×2 cm in size with a thickness of 0.7 cm is produced from a mixture of 30 g of collagen suspension with 7 g of calcium phosphate granules. The mixture is deep-frozen overnight and then briefly thawed. The mixture is subsequently freeze dried under standard conditions. Standard conditions means: freezing phase (−40° C., 1-3 h), warming phase (0° C., 1-3 h), drying phase (20° C., 12-18 h) The resulting product comprises from 98 to 99% by weight of calcium phosphate and from 1 to 2% by weight of collagen.

2. Mixture with Blood:

The resulting composite shows excellent properties on wetting with blood. It completely absorbs the blood. It shows no swelling or deformation of the composite.

3. Stability

Stability over 12 days in buffer can be demonstrated. During these 12 days, the composite remains compact and the granules are coherent.

We claim:

1. A structured composite as support for tissue engineering and implant material of bones comprising a mass of individual porous calcium phosphate granules, said composite comprising granules having a particle size of from 2 to 10 mm with macropores and micropores, where the macropores have an average diameter of from 50 to 500 µm and the micropores have an average diameter from 0.5 to 5 µm, and a collagen as a biocompatible binder, wherein said individual calcium phosphate granules are uniformly distributed in a collagen fabric formed by the collagen binder, wherein the composite cannot be compressed by pressure from adjacent connective tissue, wherein the composite is obtained by a process comprising the steps of deep-freezing, thawing and subsequent freeze-drying of a mixture comprising said calcium phosphate granules and a suspension of the collagen binder, and wherein the resulting structured composite comprises from 98 to 99 percent by weight of calcium phosphate and from 1 to 2 percent by weight of the collagen binder.

2. The composite as claimed in claim 1, wherein the collagen binder is type I collagen or a mixture of type I and III collagen.

3. The composite as claimed in claim 1, wherein the collagen binder is crosslinked.

4. The composite as claimed in claim 1, wherein said structured composite contains autologous factors.

5. The composite as claimed in claim 1, wherein said structured composite contains recombinant factors or fragments thereof.

6. The composite as claimed in claim 1, wherein said structured composite contains antibiotics.

7. The composite as claimed in claim 4, wherein said autologous factor is a growth factor, a platelet preparation, an autologous cell preparation, a cell extract, a protein preparation or a combination thereof.

8. The composite as claimed in claim 5, wherein said recombinant factor is a growth factor, an adhesion protein and/or an adhesion peptide.

9. A process for performing spinal, oral or facial surgery requiring a bone substitute or bone remodeling, comprising introducing a filling material comprising the structured composite according to claim 1 into an area requiring the bone substitute or bone remodeling.

10. A process for producing a structured composite as support for tissue engineering and implant material of bones, comprising mixing a solution or suspension of a biocompatible collagen binder with calcium phosphate granules having a particle size of from 2 to 10 mm with macropores and micropores, where the macropores have an average diameter of from 50 to 500 µm and the micropores have an average diameter from 0.5 to 5 µm; deep freezing, thawing, and subsequently freeze drying of the mixture under standard conditions, wherein the resulting structured composite comprises from 98 to 99 percent by weight of calcium phosphate and from 1 to 2 percent by weight of the collagen binder.

11. The process as claimed in claim 10, wherein the collagen binder is subsequently chemically crosslinked.

* * * * *